United States Patent [19]

Davis

[11] Patent Number: 4,872,866
[45] Date of Patent: Oct. 10, 1989

[54] MEDICAL LAVAGE APPARATUS

[76] Inventor: Richard C. Davis, 14802 Dunstan Place, Tampa, Fla. 33618

[21] Appl. No.: 292,163

[22] Filed: Dec. 30, 1988

Related U.S. Application Data

[63] Continuation of Ser. No. 95,077, Sep. 11, 1987.

[51] Int. Cl.$^4$ ............................................ A61M 5/315
[52] U.S. Cl. .................................................. 604/227
[58] Field of Search ................... 604/38, 39, 82, 92, 604/191, 227; 222/137, 145, 144.5; D. 24/24, 25, 59, 61

[56] References Cited

U.S. PATENT DOCUMENTS

| | | |
|---|---|---|
| 13,975 | 12/1855 | Buhler . |
| 386,603 | 7/1888 | Parsons . |
| 1,496,126 | 6/1924 | Livingstone . |
| 3,159,312 | 12/1964 | Van Sciver II ..................... 222/137 |
| 3,398,743 | 8/1968 | Shalit .................... 128/231 |
| 3,450,134 | 6/1969 | Willgerodt .......................... 128/214 |
| 3,818,907 | 6/1974 | Walton .............................. 128/172.2 |
| 3,828,980 | 8/1974 | Creighton et al. .................. 222/137 |
| 4,046,166 | 9/1977 | Bender ............................ 137/625.48 |
| 4,054,137 | 10/1977 | Lee et al. ............................. 128/234 |
| 4,260,077 | 4/1981 | Schroeder ........................... 604/191 |
| 4,662,868 | 5/1987 | Cambio, Jr. ............................ 604/32 |

Primary Examiner—Jerome L. Kruter
Attorney, Agent, or Firm—Griffin, Branigan & Butler

[57] ABSTRACT

A medical lavage apparatus (10) for body cavities, comprises a housing (20) having parallel irrigation and aspiration cylinders (28, 32) with plungers (24, 26) extending in bores thereof from a first end and aspiration and irrigation check valves positioned in parallel, smaller, offset, valve cylinders (46, 48) located at second ends. A septum (50) formed of intersecting semi-circular-in-cross-section baffles joins the adjacent outer ends of the irrigation and aspiration check valve cylinders so as to allow full fluid streams flowing from these outer ends to flow together at an angle. An oblong-in-cross-section, funnel-shaped, common exchange tube (22) is attached to the housing surrounding ends of both the irrigation and aspiration check valve cylinders and the septum. Inlet and outlet ports (42 and 44) are respectively positioned on the sides of the irrigation and aspiration cylinders with appropriate check valves located therein for coupling respectively to supply and waste containers (12, 16). When either of the plungers is fully inserted into its respective cylinder, a seal (80) on the end thereof covers the respective inlet or outlet port, thereby making that cylinder inoperative so as to avoid undesired fluid mixing between cylinders.

1 Claim, 2 Drawing Sheets

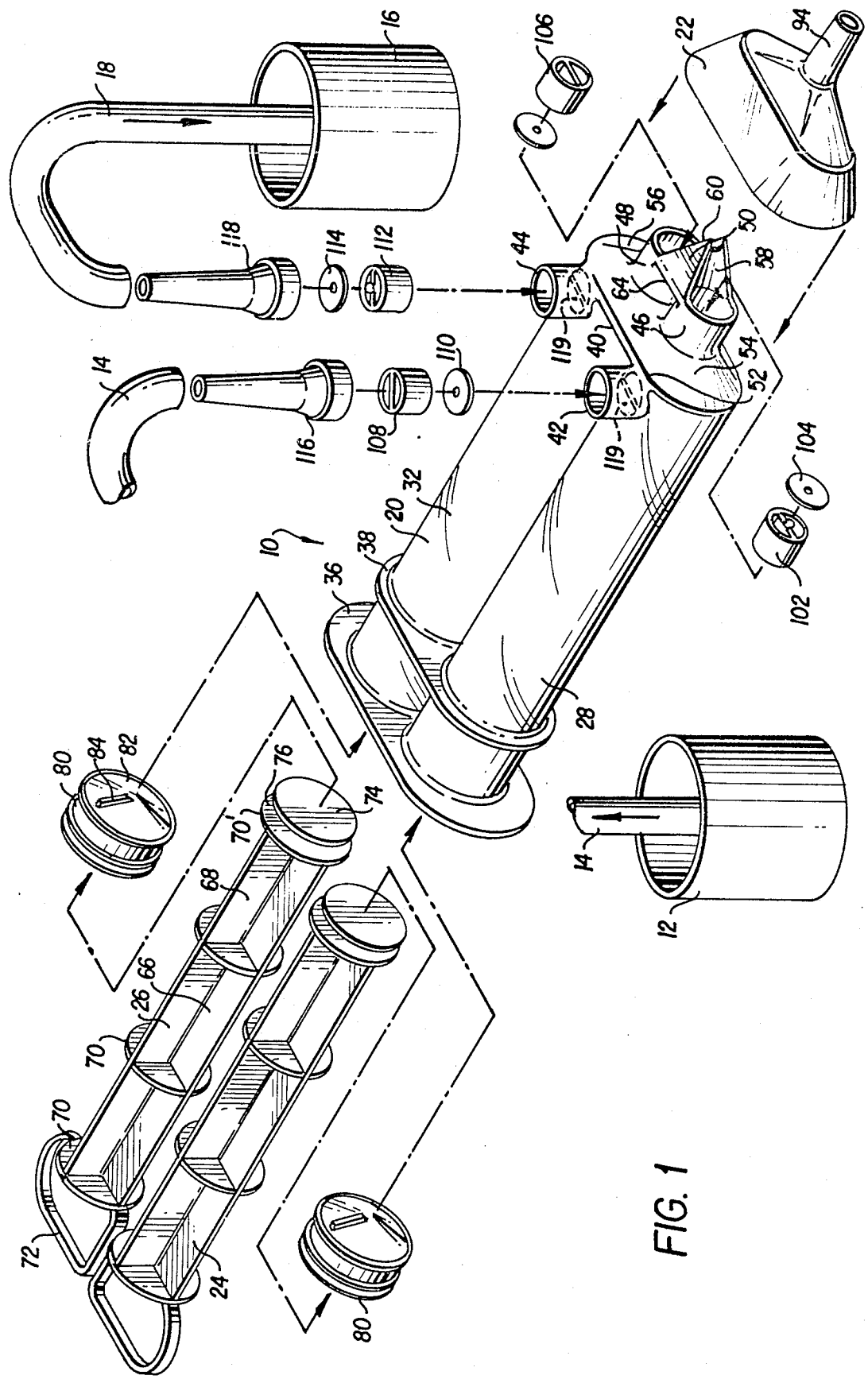

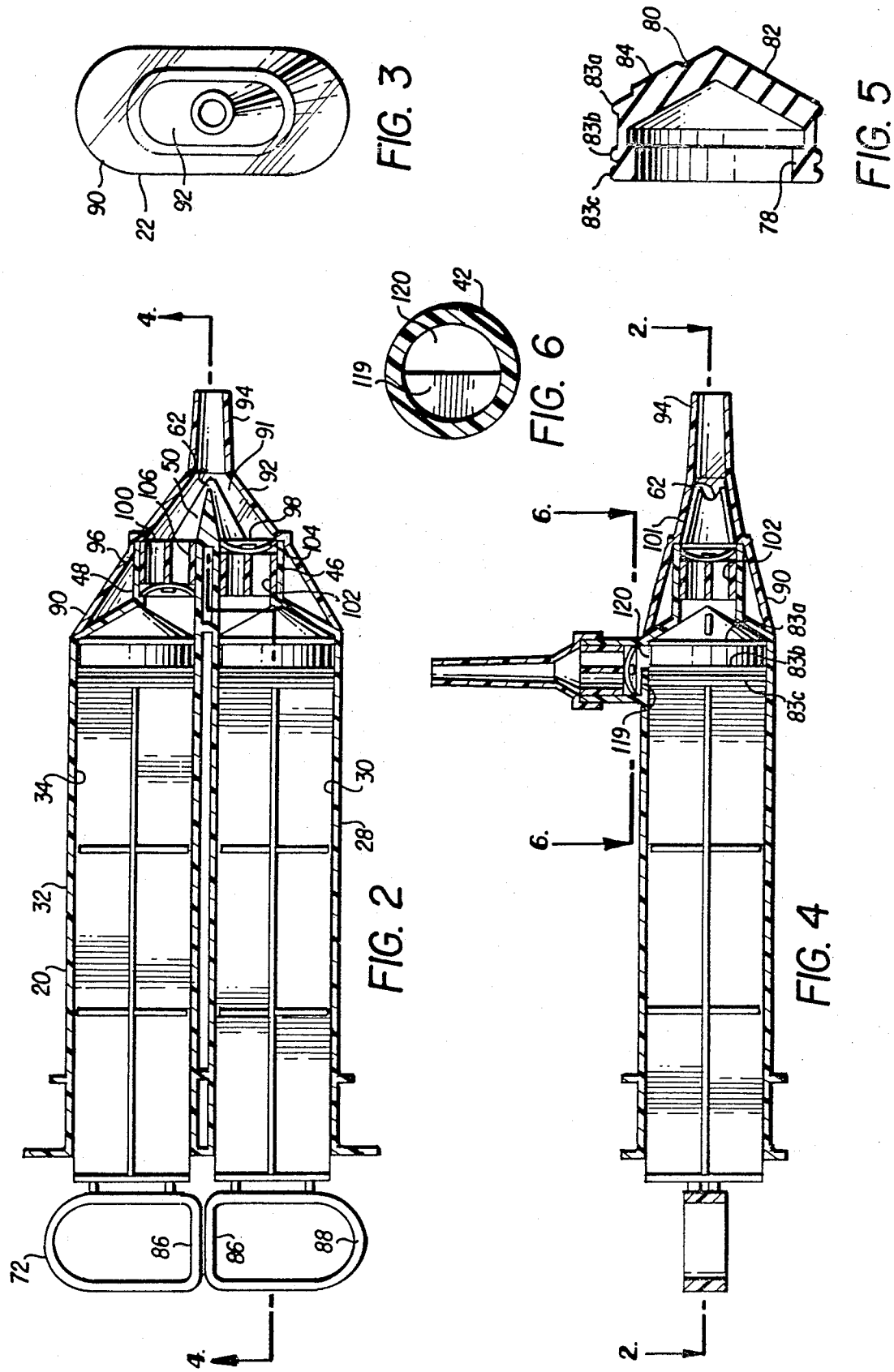

MEDICAL LAVAGE APPARATUS

This is a divisional application of Ser. No. 95,077, filed Sept. 11, 1987.

BACKGROUND OF THE INVENTION

This invention relates broadly to the art of medical lavage devices and particularly to those which can be used for quickly exchanging fluids of body cavities.

Lavage is defined as the washing out of a hollow organs by copious injection and reinjections of fluids. Gastric lavages, for example, are used for a wide variety of medical situations including poisonings, upper GI, bleeding, ulcers, etc. The normal current method of performing such a gastric lavage involves the insertion of a tube into a patient's stomach through his nose or mouth. The medical personnel conducting the lavage inject saline solution into the patient's stomach via the tube with a syringe. After waiting a few seconds, to allow mixing, this solution is sucked back through the tube with the syringe, the syringe is disconnected from the tube and the medical person performing the lavage places his or her thumb over the tube to prevent leaking of gastric contents onto the patient, the bed, the floor, or the doctor. The medical person's hands are thereby contaminated. The medical person gets a second syringe that has been filled with saline slurry just like the first, and while the first syringe is emptied in a waste pan the second syringe is used to repeat the process. This process is repeated cycle after cycle until the lavage procedure is completed. Such a procedure is extremely messy, non-sterile, and is very time consuming. It is an object of this invention to provide a lavage apparatus which is not messy to use, which allows personnel and equipment to remain sterile, and with which a lavage procedure can be quickly performed.

A number of double cylinder lavage syringes have been suggested in the past, however, none of these has achieved wide-spread popular use because they are difficult and expensive to construct, and/or because they do not operate efficiently. With regard to efficient operation, Walton (U.S. Pat. No. 3,818,907) describes a double cylinder lavage syringe in which two pistons thereof are always simultaneously operated. As the pistons are simultaneously pulled out of cylinders, a check valve system is intended to cause one cylinder to fill with a fresh solution while the other cylinder sucks fluid out of a body organ. Both of the cylinders are attached to a common tube which is extended into the organ. However, it appears that this system is complicated to construct and does not prevent a "bleed through" of fluid into the improper cylinder, that is, a cross-mixing of clean and waste fluids, especially if the lavage tube becomes clogged. Thus, it is an object of this invention to provide a lavage apparatus which not only is relatively easy and inexpensive to construct but which also prevents "cross-mixing". With regard to ease of construction, it is an object of this invention to provide a lavage device which is so economical to construct that it can be disposable.

U.S. Pat. Nos. 13,975 to Buhler, 3,818,907 to Walton and 3,159,312 to Sciver, II all disclose systems wherein a common tube is connected to side-by-side cylinders via Y connected tubes away from the cylinders. Such an arrangement is not only complicated and awkward to use, but provides inefficiencies and allows mixing of contaminated and uncontaminated fluids as well. Thus, it is an object of this invention to provide a lavage apparatus which has a common exchange tube as a rigid element attached to a housing which prevents mixing and provides highly efficient pump action.

Yet another difficulty with some of the prior art lavage systems is that their structures, including check valves used therewith, are difficult and expensive to construct. It is an object of this invention to provide a lavage apparatus whose main components can be easily molded of resinous plastic and whose elements can be easily combined.

SUMMARY

According to principles of this invention, a lavage apparatus includes a rigid housing defining side-by-side, parallel irrigation and aspiration cylinders in which plungers are inserted from first ends thereof. The irrigation and aspiration cylinders have respectively irrigation and aspiration check valves at second ends thereof and inlet and outlet check valves at sides thereof. An anti venturi septum extends to an intersecting line from the second ends of the cylinders. This septum comprises two tapered, semi-circular-in-cross-section, baffles which meet at a sharp V-shaped apex which also forms a U-shaped intersection line to provide a full opening between a separate common exchange tube and both cylinders. The separate common exchange tube, with the common nozzle, is attached to the housing surrounding the second ends of the cylinders and said septum. The internal size of the nozzle is about the same size as inlet and outlet openings at the sides of the cylinders.

BRIEF DESCRIPTION OF THE DRAWINGS

The foregoing and other objects, features and advantages of the invention will be apparent from the following more particular description of the preferred embodiment of the invention as illustrated in the accompanying drawings in which reference characters refer to the same parts throughout the different views. The drawings are not necessarily to scale, emphasis instead being placed upon illustrating principles of the invention in a clear manner.

FIG. 1 is a isometric, exploded, view of the lavage apparatus of this invention and further includes waste and source containers and tubes to be used with the lavage apparatus;

FIG. 2 is a top, partially cross-sectional, view of the lavage apparatus of FIG. 1 taken on line 2—2 in FIG. 4;

FIG. 3 is an end view of the lavage apparatus of FIG. 2;

FIG. 4 is a side, partially sectional, view of the apparatus of FIG. 2, taken on lines 4—4;

FIG. 5 is a side sectional view of a plunger seal which is at the end of the plungers of the lavage apparatus of FIG. 1; and, FIG. 6 is a sectional view taken on line 6—6 in FIG. 4.

DESCRIPTION OF THE PREFERRED EMBODIMENT

The lavage apparatus 10 is shown in FIG. 1 for use with a supply container 12, supply tube 14, a waste container 16 and a waste tube 18.

The lavage apparatus 10 comprises a rigid housing 20, a common exchange tube 22, an irrigation plunger 24, an aspiration plunger 26, and a system of seals and valves associated therewith.

Looking first at the rigid housing 20, this housing is molded as one piece of a medical grade, translucent styrene acrylonitrile plastic. The rigid housing 20 has an irrigation cylinder 28 defining an irrigation-cylinder bore 30, an aspiration cylinder 32 defining an aspiration-cylinder bore 34, first and second supporting flanges 36 and 38 holding together first ends of the irrigation and aspiration cylinders 28 and 32, a third flange 40 holding together second ends of the irrigation and aspiration cylinders 28 and 32, an inlet port 42 located near the second end of the irrigation cylinder 28 an outlet port 44 located near the second end of the aspiration cylinder 32, an irrigation check-valve cylinder 46 located at the end of the irrigation cylinder 28 and an aspiration check-valve cylinder 48 located at the second end of the aspiration cylinder 32, and an anti-venturi septum 50 joining the second ends of the irrigation and aspiration check-valve cylinders 46 and 48. As can be seen in FIG. 1, the first, second, and third flanges 36, 38, and 40 hold the irrigation cylinder 28 and the aspiration cylinder 32 in a side-by-side, parallel, relationship. The bores 30 and 34 of the respective irrigation and aspiration cylinders 28 and 32 are the same size, each providing approximately 160 cc's in actual stroke volume.

The inlet and outlet ports 42 and 44 are close to the second ends 52 of the irrigation and aspiration cylinders 28 and 32 in the form of small, equal sized, valve cylinders extending perpendicular to axes of the irrigation and aspiration cylinders 28 and 32. This increases the turbulance of the fluid flow allowing for increased mixing and dissolution of the aspirated contents thereby reducing valve clogging.

It can be seen in FIG. 1 that the equal sized irrigation and aspiration check-valve cylinders 46 and 48 are connected to their respective irrigation and aspiration cylinders 28 and 32 by tapered bonnets 54 and 56, respectively so as to be close to, and parallel with one another. In this respect, the circumference of the check-valve cylinders 46 and 48 is about half that of the irrigation and aspiration cylinders 28 and 32 and their axes are offset from those of the irrigation and aspiration cylinders 28 and 32 so that the irrigation and aspiration check-valve cylinders 46 and 48 are close to one another with their bores aligned with the irrigation and aspiration cylinder bores 30 and 34.

The septum 50 has an irrigation baffle 58 and an aspiration baffle 60, each of which is semi-circular in cross-sectional shape. These baffles intersect at an outer tip 62 which forms a U-shaped line. In this regard, the septum baffles 58 and 60 are only positioned on the inside sides of the check valve cylinders 46 and 48 so as to guide fluid from and to the check-valve cylinders 46 and 48. A fourth flange 64 interconnects the outer ends of the check-valve cylinders 46 and 48 and forms an oval with these outer ends.

The plungers 24 and 26 are molded to be identical, each having shafts comprised of crossed slats 66 and 68 supported by intermediate ribs 70. Also molded integral therewith are finger-engaging portions 72 and seal mounting ribs 74. The seal-mounting ribs 74 are separated from the last supporting ribs 70' by a space 76 into which internally directed ribs 78 of seals 80 are inserted (see FIG. 5). Each seal 80 has a cone-shaped end 82 with small ridges 84 thereon. There are three cylinder-bore contacting rings 83a, b, and c on the outer surface thereof.

It should be noted from FIGS. 1 and 2 that the finger-engaging portions 72 of the plungers 24 and 26 are respectively turned so that they provide mirror images, one of the other. In this respect, the finger-engaging portions 72 are not geometrical, being flat at first sides 86 thereof and rounded at second sides 88 thereof. The reason for this is so that the first sides 86 can be as close together between two adjacent fingers as possible where it is desirable to operate the syringes simultaneously. Thus, although the plungers are not connected, these finger engaging portions are designed to allow easy use of one of the plungers or both as is desired. This allows one to "prime the pump", so to speak, with the irrigation half of the system prior to beginning the lavage.

The common exchange tube 22 is oblong, or oval, in cross section as can be seen in FIG. 3 to thereby form an oblong chamber 91 in which fluid flows to and from the irrigation and aspiration cylinders 28 and 32. The common exchange tube 22 includes an apron portion 90, a manifold portion 92, a common nozzle portion 94, and an attachment ridge 96. The attachment ridge 96 is of a size to sealingly fit about the side-by-side irrigation and aspiration check-valve cylinders 46 and 48 and the fourth flange 64 which joins them. In use, these members are held together by sonic welding or by an adhesive. The apron portion 90 makes the entire apparatus more streamlined in appearance and for handling, however, it is not necessary for operation of the lavage apparatus.

The manifold portion 92 encloses and seals with outer ends 98 and 100 of the irrigation and aspiration check-valve cylinders 46 and 48 as well as the septum 50, as can be seen in FIG. 2, so that all material flowing to and from the outer ends 98 and 100 are guided by the septum 50 and the manifold portion 92. Similarly, all fluids flowing to and from the manifold portion 92 flow through the common nozzle 94. It should be noted that the septum 50 is so arranged and designed that fluid streams flowing from the irrigation check-valve cylinder 46 will be directed into the nozzle 94 and fluid flowing from the nozzle 94 will be directed to the aspiration check-valve cylinder 48 without restriction and without causing undue turbulence. In this manner, such fluid streams are not caused to cross mix. The U-shaped outer tip line 62 particularly aids in avoiding undue cross mixing by not causing a venturi restriction to create a negative pressure in the manifold portion 94 which improperly opens a check-valve. Sidewalls of the septum 50 press against interior surfaces of the manifold at 101 to create a seal therebetween.

With regard to the check valves, an irrigation check valve 102 has a cylinder outer wall with a cross-wall carrying a resilient membrane 104 thereon which flexes open when pressure is exerted from the irrigation-cylinder bore 30 toward the nozzle 94 but closes when pressure is exerted in the opposite direction. An aspiration check valve 106 in the aspiration check-valve cylinder 48 operates in a similar but opposite manner. An inlet check valve 108, with an attached membrane 110, allows fluid to flow into the irrigation cylinder 28, but does not allow flow from the irrigation cylinder 28. Similarly, an outlet check-valve 112 allows fluid flow from the aspiration cylinder 32, however, it does not allow flow therein. Funnel-like inlet and outlet adaptors 116 and 118 are respectively attached to the inlet port 42 and the outlet port 44.

Regarding the inlet and outlet ports 42 and 44, these are each restricted by a shelf 119 (FIG. 4) which makes an actual port opening 120 have an elongated (semicircular) shape as can be seen in FIG. 6 and have the same cross-sectional area as the bore of the nozzle 94. The approximate matching of these sizes balances pressures within the system so as to avoid improper opening of the check-valves during operation and thereby avoid cross mixing of contaminated and pure fluids. The shelves 119 have the additional purpose of creating elongated port openings 120 which allows the openings 120 to be fully sealed by the relatively-close-together contacting rings 83a, b, and c when the respective plungers 24 and 26 are fully depressed, as shown in FIG. 4. Still further, the shelf 119 at the aspiration outlet port 44 tends to break up solids which might otherwise jam the membrane 114. Finally, the shelves 119 allow rather large membrane type check-valves to be used with necessarily smaller valve openings 120. These larger check valves are not as vulnerable to jamming as smaller ones.

All of the various rigid components of this invention can be constructed of a rigid hard resinous plastic such as styrene acrylonitrile.

In operation of the lavage apparatus of this invention, the rigid housing 20, the two plungers 24 and 26, the common exchange tube 22, and the various check valve cylinders 102, 106, 108, and 112 and the inlet and outlet adaptors 116 and 118 are molded of hard resinous plastic. In this respect, all of the check-valves are the same size so as not to require more than one mold for these elements. The plunger seal 80 and the various check-valve membranes are molded, or purchased off-the-shelf. The plunger seals 80 are attached to plungers 24 and 26 and the various check-valve membranes are attached to knobs on the check-valve cylinders 104, 106, 108, and 112. The check valve cylinders are then attached by sonic welding in their respective positions to the rigid housing 20 as is depicted in the exploded view of FIG. 1. Thereafter, the attachment ridge 96 of the common exchange tube 22 is sealingly adhered to the irrigation and aspiration check valve cylinders 46 and 48 and the flange 64 which adjoins these two ridges. The various valves cannot be easily serviced, but that is not necessary since the lavage apparatus is designed to be a single use disposable product.

To utilize the lavage apparatus 10 one places a saline liquid in the supply container 12 which is joined via a supply tube 14 and the inlet adapter 116 to the inlet port 42. The waste container 16 is similarly attached via tube 18 and outlet adapter 118 to the outlet port 44. The saline solution is to be instilled into a body cavity, left for a short length of time and then sucked out. A tube (not shown) is attached to the nozzle 94 of the common exchange tube 22 which is inserted through an opening in the human body into the organ to be lavaged. Where fluid from more than one irrigation cylinder 28 is to be inserted into the organ before any is aspirated, the aspiration plunger 26 is driven completely into the aspiration cylinder 32 as is depicted in FIGS. 2 and 4. In this position, the aspiration plunger seal 80 completely seals the opening 120 of the outlet port 44. Thus, while the aspiration plunger 26 is left in this position, no fluid can flow through the outlet port 44. With the aspiration plunger 26 so situated, the irrigation plunger 24 is pulled outwardly to cause a vacuum in the irrigation cylinder 28. This vacuum respectfully opens the membrane 110 of the inlet check-valve 108 and closes the membrane 104 of the irrigation check-valve 102. Thus, fluid is sucked from the supply container 12 into the irrigation cylinder 28. Thereafter, the irrigation plunger 24 is driven into the irrigation cylinder 28 which closes the inlet check valve 108, opens the irrigation check valve 102, and drives fluid out of the irrigation cylinder 28 into the manifold portion 92 of the common exchange tube 22 and out the nozzle 94 of the common exchange tube 22. In this respect, the irrigation baffle 58 of the septum 50 guides this fluid to ensure that it enters the nozzle 94 rather than being driven through the aspiration check-valve cylinder 48 to open the aspiration check-valve 106 and thereby drive the plunger 26 from its blocking position. The irrigator plunger 24 is moved in and out until the body cavity has the right amount of fluid in it.

After the irrigation fluid has been left in the body organ for a period of time, the irrigation plunger 24 is driven fully into the irrigation cylinder 28 so that seal 80 cover the openings 120 of the inlet port 42 thereby not allowing flow of fluid through this port. Now the aspiration plunger is pulled out and pushed in, thereby sucking contaminated fluid from the body organ through the nozzle 94, and the aspiration check-valve cylinder 48, into the aspiration cylinder 32, driving the contaminated waste fluid out of the outlet port 44 into the waste container.

Ordinarily, most body organs requiring lavage will be of such a size as to hold multiple loads of the irrigation cylinder 28, with the skill of an operator protecting against over distension of a cavity. Once the appropriate amount of irrigant is instilled, the irrigation and aspiration plungers 24 and 26 will be gripped together and moved in and out simultaneously thereby maintaining a constant steady-state volume of fluid flow in the organ. On the out strokes the irrigation cylinder 28 will be loaded with fresh fluid from the supply container 12 and the aspiration cylinder 32 will be loaded with contaminated waste from the organ. On the in strokes the fresh fluid in the irrigation cylinder 28 will be forced into the organ and the contaminated waste fluid in the aspiration cylinder 32 will be forced into the waste container 16. During these strokes, since the openings 120 of the inlet and outlet ports 42 and 44 have the same cross-sectional size as the internal bore of the nozzle 94, the pressures applied at each of these by the equal size plungers 24 and 26 are approximately equal, there being only a small drop across each of the various valves to cause them to act as check valves in the appropriate directions. Similarly, the shape of the U-shaped outer tip line 62 of the septum 50 does not cause undue venturi or eddy effects which create undue changes in pressure at the nozzle 94 to improperly open the irrigation and aspiration check valves 102 and 106 to cause a mixing.

A unique feature of the design of this lavage apparatus is that it can be used to clear itself of debris. In this regard, the most likely occlusion will occur on the aspiration side of the device because it is the part which is exposed to particulate matter. If a clog should develop, one can clear it by pulling back on the aspiration plunger 26 until the outlet port 44 is open, crimping of the tube attached to the nozzle 94, and pumping the irrigation plunger 24 in and out to force fresh fluid through the aspiration check valve 106 and the outlet check valve 112. The tube attached to nozzle 94 can be cleared by pushing the aspiration plunger fully inward thereby sealing the port opening 120 of outlet port 44 then forcefully operating the irrigation plunger 24.

It can be appreciated by those skilled in the art that the lavage apparatus described herein is relatively easy to manufacture and use but yet allows non-messy lavaging of organs. Medical personnel can perform lavage procedures without the lavage liquid escaping outside the system and therefore not contaminating lavage personnel, a patient, nor surrounding areas and not otherwise causing an unsanitary or disagreeable problem.

The designs of the smaller, offset, irrigation and aspiration check-valve cylinders 46 and 48, the pointed plunger seals 80 and the common exchange tube 22 which is welded directly to the housing 20 creates a minimum of "dead space" between the irrigation and aspiration check valve cylinders 46 and 48 and the nozzle 94 which improves pump efficiency.

The design of the septum 50 prevents undue eddy and venturi effects.

Although this invention has been described with reference to a particular structure, it will be understood by those of ordinary skill in the art that other structural elements could also be used.

The embodiments of the invention in which an exclusive property or privilege are claimed are defined as follows:

1. A medical lavage syringe device for irrigating and aspirating a body cavity, said device comprising:

a rigid housing defining an irrigation cylinder with an elongated irrigation bore and an aspiration cylinder with an elongated aspiration bore, said bores being substantially parallel and side-by-side, said irrigation and aspiration cylinder bores each being open and unconnected at first ends thereof, said rigid housing further defining respectively an inlet port and an outlet port in said respective irrigation and aspiration cylinders intermediate first and second ends thereof;

a common tube configuration coupling second ends of said irrigation and aspiration cylinders to a common nozzle;

an irrigation plunger and an aspiration plunger having first ends for respectively fitting into said first open ends of said irrigation and aspiration cylinders and having seals at said first ends thereof for making sealing, sliding contact with internal cylinder surfaces of said respective bores and including hand-engaging portions at second ends outside the cylinders for engaging a hand and thereby being moved into and out of their respective bores by said hand;

a system of check-valves comprising an inlet check-valve located at said inlet port for allowing the flow of fresh irrigation fluid into said inlet port but hindering the flow of fluid from said inlet port, an outlet check-valve located at said outlet port for allowing the flow of aspiration fluid from said outlet port but hindering the flow of fluid into said outlet port, an irrigation check-valve located at said irrigation bore between said inlet port and said common exchange tube for allowing flow of irrigation fluid from said irrigation bore into said common exchange tube but for hindering the flow of fluid from said common exchange tube into said irrigation bore and an aspiration check-valve located at said aspiration bore between said outlet port and said common exchange tube for allowing flow of irrigation fluid from said common exchange tube into said aspiration bore but hindering flow in the opposite direction;

said hand-engaging portions of said irrigation and aspiration plungers having closed, side-by-side, loop configurations, said closed loops being in a common plane and said loops having adjacent sides when are relatively-straight, parallel-to-axes-of-elongation-of-said-bores, said sides positioned close to each other to allow a user to grip both hand engaging portions with fingers of one hand while simultaneously moving the irrigation and aspiration plungers into and out of the irrigation and aspiration cylinders while maintaining these fingers close together.

* * * * *